United States Patent
Hong et al.

(10) Patent No.: US 11,717,658 B2
(45) Date of Patent: Aug. 8, 2023

(54) SKIN CARE DEVICE (71) Applicant: LG ELECTRONICS INC., Seoul (KR)

(72) Inventors: Sungho Hong, Seoul (KR); Nayoung Kim, Seoul (KR); Sangwon Kim, Seoul (KR); Yongju Yang, Seoul (KR); Gueisam Lim, Seoul (KR); Dongwon Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 277 days.

(21) Appl. No.: 16/760,877

(22) PCT Filed: Nov. 1, 2018

(86) PCT No.: PCT/KR2018/013166
§ 371 (c)(1),
(2) Date: Apr. 30, 2020

(87) PCT Pub. No.: WO2019/088724
PCT Pub. Date: May 9, 2019

(65) Prior Publication Data
US 2021/0170150 A1   Jun. 10, 2021

(30) Foreign Application Priority Data

Nov. 3, 2017 (KR) .................... 10-2017-0146109

(51) Int. Cl.
*A61M 37/00* (2006.01)
*A61H 23/02* (2006.01)
(Continued)

(52) U.S. Cl.
CPC ......... *A61M 37/00* (2013.01); *A61H 23/0245* (2013.01); *A61H 2201/0153* (2013.01);
(Continued)

(58) Field of Classification Search
CPC .............. A61M 37/00; A61M 37/0092; A61M 2037/0007; A61N 1/303; A61N 1/044;
(Continued)

(56) References Cited

U.S. PATENT DOCUMENTS 2,891,194 A * 6/1959 McStrack ................ H01C 7/12
315/36
2004/0220622 A1 * 11/2004 Bernabei .............. A61H 39/002
607/3

(Continued)

FOREIGN PATENT DOCUMENTS

EP    1943999 A1 * 7/2008 ......... A61H 23/0245
KR   1020040060719    7/2004
(Continued)

OTHER PUBLICATIONS

English translation of Hyeon et al. (KR 2011/0020405) (Year: 2011).*

(Continued)

*Primary Examiner* — Nilay J Shah
(74) *Attorney, Agent, or Firm* — Lee Hong Degerman Kang & Waimey (57) ABSTRACT

In order to achieve the above or other aims, according to one aspect of the present disclosure, a skin care device is provided which comprises: a body comprising a grip section for a user to hold, and a head section positioned at the end of the grip section; a plurality of skin-contacting plates positioned at the end of the head section; a plurality of oscillators for providing oscillations to each of the skin-contacting plates; and a control unit which supplies an electrical current to the skin-contacting plates and controls the oscillators, wherein the positive electrode and the negative electrode of the control unit are respectively connected to different skin-contacting plates.

7 Claims, 6 Drawing Sheets

(51) Int. Cl.
*A61N 1/30* (2006.01)
*A61N 1/04* (2006.01)

(52) U.S. Cl.
CPC .... *A61H 2201/10* (2013.01); *A61H 2205/022* (2013.01); *A61M 37/0092* (2013.01); *A61M 2037/0007* (2013.01); *A61N 1/044* (2013.01); *A61N 1/303* (2013.01)

(58) Field of Classification Search
CPC ........ A61N 1/325; A61N 1/327; A61N 1/328; A61H 23/0245; A61H 2201/10; A61H 2201/0153; A61H 2205/022
See application file for complete search history.

(56) References Cited

U.S. PATENT DOCUMENTS

| | | | | |
|---|---|---|---|---|
| 2005/0049642 | A1* | 3/2005 | Bernabei | A61N 1/325 607/3 |
| 2005/0107832 | A1* | 5/2005 | Bernabei | A61H 23/02 607/3 |
| 2006/0034904 | A1* | 2/2006 | Weimann | A61K 9/7092 424/449 |
| 2009/0230823 | A1* | 9/2009 | Kushculey | B06B 1/0637 310/366 |
| 2011/0170934 | A1* | 7/2011 | Ki | B05B 11/3052 401/118 |
| 2012/0089052 | A1* | 4/2012 | Zhou | A61H 23/0245 601/2 |
| 2013/0231592 | A1* | 9/2013 | Lee | A61N 7/00 601/2 |

FOREIGN PATENT DOCUMENTS

| | | | |
|---|---|---|---|
| KR | 10-2008-0067309 | | 7/2008 |
| KR | 1020080067308 | | 7/2008 |
| KR | 20110020405 | A * | 3/2011 |
| KR | 10-2012-0037894 | | 4/2012 |
| KR | 20160070544 | A * | 6/2016 |
| KR | 1020160070544 | | 6/2016 |
| KR | 1020160086026 | | 7/2016 |
| KR | 1020170075129 | | 7/2017 |

OTHER PUBLICATIONS

PCT International Application No. PCT/KR2018/013166, Written Opinion of the International Searching Authority dated Apr. 4, 2020, 19 pages.
Korean Intellectual Property Office Application No. 10-2017-0146109, Office Action dated Jul. 22, 2022, 6 pages.

* cited by examiner

SKIN CARE DEVICE

CROSS-REFERENCE TO RELATED APPLICATIONS

This application is the National Stage filing under 35 U.S.C. 371 of International Application No. PCT/KR2018/013166, filed on Nov. 1, 2018, which claims the benefit of earlier filing date and right of priority to Korean Application No. 10-2017-0146109, filed on Nov. 3, 2017, the contents of which are all hereby incorporated by reference herein in their entirety.

TECHNICAL FIELD

The present disclosure relates to a skin care device provided in further consideration of user's convenience.

BACKGROUND ART

The number of people who are interested in appearance is increasing day by day, and the number of people who regularly take care of their skin by attending dermatologists and skin care centers as well as cosmetics is increasing. However, the burden on consumers is increasing because it costs a lot to use a dermatologist or a skin care center, and self-skin care devices are emerging to make it easier to manage.

In the past, no portable type of device was available to individuals, but recently, many portable care devices have been commercialized due to the development of wireless communication and the miniaturization of parts.

Device for skin beauty is implemented in various ways. The skin is subject to fine stimulation and changes in the activities of cells, which can lead to improvement of wrinkles and whitening. In addition, skin care devices that maximize the performance of cosmetics by applying cosmetics to the skin and assisting absorption, vibrates the skin to promote the penetration of cosmetics between skin cells. Ultrasound can also massage the skin to relax muscles and increase elasticity.

There is a problem in which the absorption efficiency varies depending on the ingredients of cosmetics, as simply vibrating the skin does not absorb all the ingredients of cosmetics.

Skin care devices that promote the absorption of cosmetics by applying electric current in an electrical way require the user to hold the electrodes located on the handle in order to flow current to the user's body, so the position of the hand holding the handle is limited and it is difficult for a third party to use the skin care device for management.

DISCLOSURE

Technical Task

The technical task of the present disclosure is to provide a skin care device that can increase the absorption rate of cosmetics containing various ingredients.

Technical Solutions

In one technical aspect of the present disclosure, provided herein is a skin care device, including a body including a grip part gripped by a user and a head part located at an end portion of the grip part, a plurality of skin contact plates located at an end portion of the head part, a plurality of vibrators providing vibration to the skin contact plate, and a controller supplying current to the skin contact plate and controlling the vibrator, wherein + pole and − pole of the controller are connected to the skin contact plates different from each other, respectively.

Each of a plurality of the vibrators may provide the vibration of a different frequency.

The skin contact plate may include a first skin contact plate in a circular shape and a second skin contact plate in a ring shape located on a circumference of the first skin contact plate.

The skin care device may further include a support plate located on a backside of the second skin contact plate in a manner of being spaced apart in a prescribed distance and a connecting leg connecting the support plate and the second skin contact plate together. And, the vibrator may include a first vibrator providing the vibration by being coupled to a backside of the first skin contact plate and a second vibrator seated on the support plate to provide the vibration to the second skin contact plate.

The connecting leg may have a cylindrical shape connected to the second skin contact plate in the ring shape at a plurality of points and electric wire connecting the first vibrator, the first vibration plate and the controller may pass through the connecting leg.

A plurality of the skin contact plates may form sector shapes having the same diameter and may be disposed in a manner of forming a circular shape.

A plurality of the skin contact plates may be inclined at different angles, respectively.

The skin care device may further include a connecting part connecting the skin contact plates in between and having a variable shape.

The skin contact plate may include conductive material and the connecting part may include insulating material to electrically divide a plurality of the skin contact plates from each other.

The connecting part may be formed of ductile material.

Advantageous Effects

A skin care device according to the present disclosure is described as follows.

According to at least one of embodiments of the present disclosure, the absorption rate of cosmetics mixed with various ingredients can be increased.

According to at least one of embodiments of the present disclosure, the inconvenience that users have to hold onto and use separately equipped electrodes can be solved.

Other objects and further scope of applicability of the present disclosure will become apparent from the detailed description given below. It is to be understood, however, that the detailed description and specific examples such as preferred embodiments of the disclosure are given by way of illustration only, since it is obvious to those skilled in the art that various changes and modifications can be made within the spirit and scope of the disclosure.

BEST MODE FOR DISCLOSURE

Devices for skin care or treatment are implemented in a variety of ways. The skin is subjected to minute stimuli to change the activity of cells, which can lead to improved skin effects on wrinkles, whitening, etc.

One of the most representative forms is the noninvasive form of giving electrical impulses to the skin, or the invasive form of giving physical stimuli.

Although a device of an individually portable type was not available conventionally, as the development of wireless communication and the downsizing of components have become more common in recent years, portable care devices are popularly commercialized.

Figure 1:
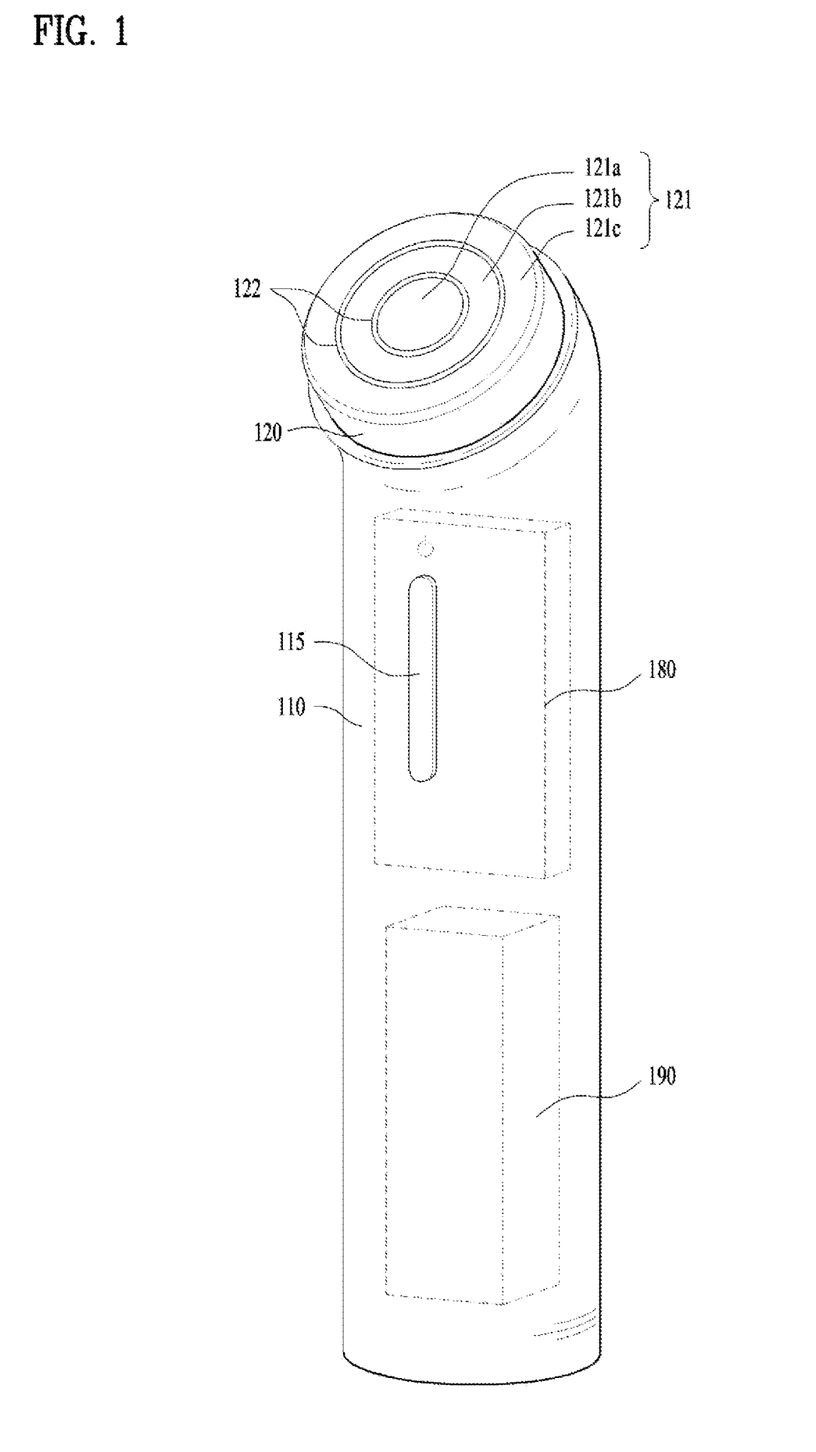
FIG. 1 is a perspective diagram of a skin care device working on a deep part and surface of a human skin related to the present disclosure.

FIG. 1 is a perspective diagram of a skin care device 100 working on a deep part and surface of a human skin related to the present disclosure. The skin care device 100 according to the present disclosure includes a grip part 110 gripped by a user with a hand and a head part 120 having a skin contact plate 121 located at an end portion of the grip part 110 to contact with a user's skin. When a user applies a force to the skin contact plate 121 to touch a face, the grip part 110 and the head part 120 may form angles between 90~180 degrees for facilitation.

The grip part 110 may include a space inside to receive a battery 190 as a power supply part and a printed circuit board 180 as a controller therein, and a manipulating part 115 for manipulation of power-on/off may be provided to an outer surface of the grip part 110. Additionally, a display part displaying a current operational state may be included. The display part may employ a way of displaying a color of a lamp simply or a way of displaying texts or symbols like LCD.

A power connection part for connecting an external power source may be included in the grip part 110. If the battery 190 is not provided, the power connection part may adopt a way of supplying permanent power. If the battery 190 is provided, the power connection part plays a role in charging the battery 190. The charging may be performed in a manner of supplying power by connecting a charger supplied with external power through a terminal or using wireless charging.

As the head part 120 is directly touched with user's skin, it should be equipped with a waterproof structure to prevent particles from entering an inside of the head part 120. The head part 120 includes a skin contact plate 121 contacting with user's skin. And, the skin care device 100 of the present disclosure is characterized in having a plurality of the skin contact plates 121.

In the related art, a single skin contact plate is used to supply ultrasonic waves of a single wavelength, but the skin care device 100 of the present disclosure is characterized in having the head part 120 that provides vibrations in various ultrasonic bands owing to the difference in wavelength having a good absorption rate depending on the ingredients of cosmetics.

As shown in FIG. 1, a first skin contact plate 121a and a second skin contact plate 121b located around a circumference of the first skin contact plate 121a in a ring shape are provided. And, a third skin contact plate 121c located around a circumference of the second skin contact plate 121b may be provided. Moreover, two or more skin contact plates 121 may be provided. Each of the skin contact plates 121 may apply ultrasonic waves on different frequency bands by vibrators vibrating in different wavelengths, respectively. For example, a first vibrator 130a may vibrate with ultrasonic wave of 280 kHz, a second vibrator 130b may vibrate with ultrasonic wave of 350 kHz, and a third vibrator 130c may vibrate with ultrasonic wave of 1 MHz.

A connecting part 122 of ductile material may be provided between the skin contact plates 121, and is capable of a waterproof function to prevent water and the like from flowing into a gap between the connecting part 122 and the skin contact plate 121. The skin contact plate 121 may be connected using a structure such as a hinge. In this case, it is necessary to perform waterproof treatment between the skin contact plates 121.

Figure 2:
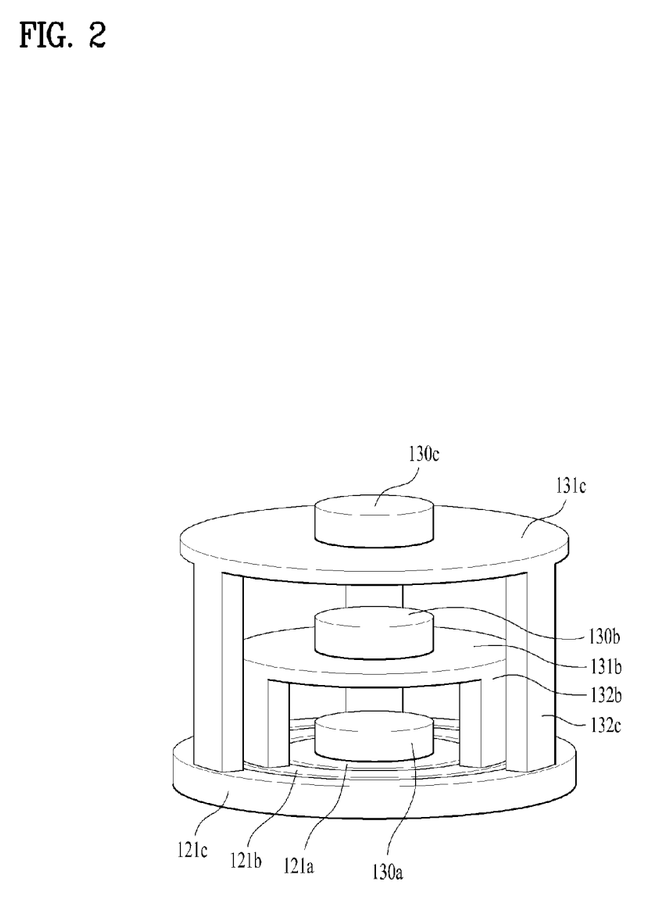
FIG. 2 is a diagram showing one embodiment of an inside of a head part of a skin care device related to the present disclosure.
Figure 3:
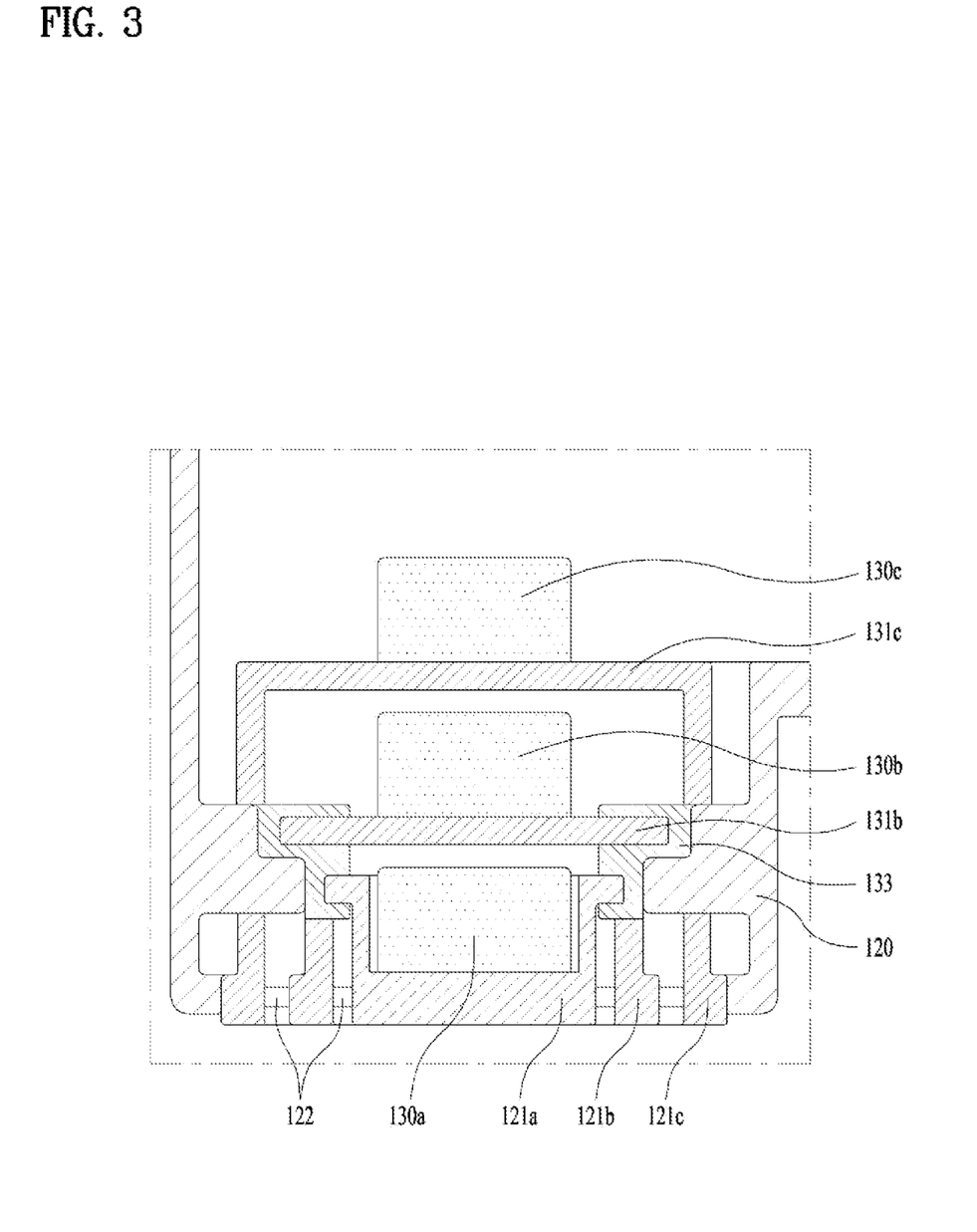
FIG. 3 is a diagram showing one embodiment of a head part of a skin care device related to the present disclosure.

FIG. 2 is a diagram showing one embodiment of an inside of the head part 120 of the skin care device 100 related to the present disclosure, and FIG. 3 is a cross-sectional diagram showing one embodiment of the head part 120 of the skin care device 100 related to the present disclosure. Since each of the second and third skin contact plates 121b and 121c has an sufficient space for coupling an vibrator thereto except the first skin contact plate 121a located at the center of the skin contact plates 121 disposed in a concentric circle shape [FIG. 1], a second vibrator 130b and a third vibrator 130c may be disposed in a second vertical direction [FIG. 2, FIG. 3].

A first support plate 131b connected to the second skin contact plate 121b through a connecting leg 132 and a second support plate 131c connected to the third skin contact plate 121c through the connecting leg 132 are included. Since the first support plate 131b is smaller than the second support plate 131c, it may be located inside the connecting leg 132 connecting the second support plate 131c and the third skin contact plate 121c together. The second vibrator 130b applying vibration to the second skin contact plate 121b may be seated on the first support plate 131b, and the third vibrator 130c applying vibration to the third skin contact plate 121c may be seated on the second support plate 131c. The connecting leg 132 is not formed in a cylindrical shape but has a shape in which a plurality of legs are connected together, whereby electric wires connecting the vibrators, the skin contact plates 121 and the printed circuit board may be disposed between the connecting legs 132.

Each of the support plates 131b and 131c may include a fixing part 133 formed of ductile material provided to a case forming an exterior of the head part 120 so as to be stably fixed thereto. As the connecting part 122 located between the skin contact plates 121 or the fixing parts are formed of the ductile material, it is able to reduce the effect caused to another skin contact plate 121 by the vibration generated from each vibrator.

Figure 4:
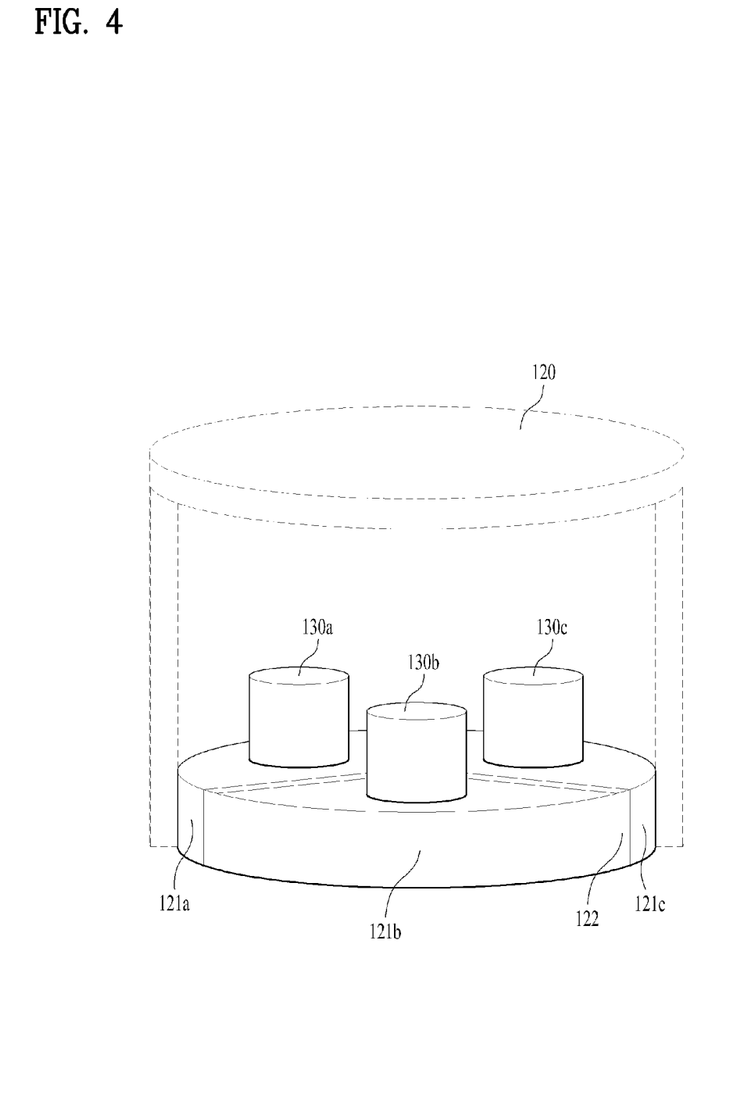
FIG. 4 is a diagram showing another embodiment of a head part of a skin care device related to the present disclosure.
Figure 5:
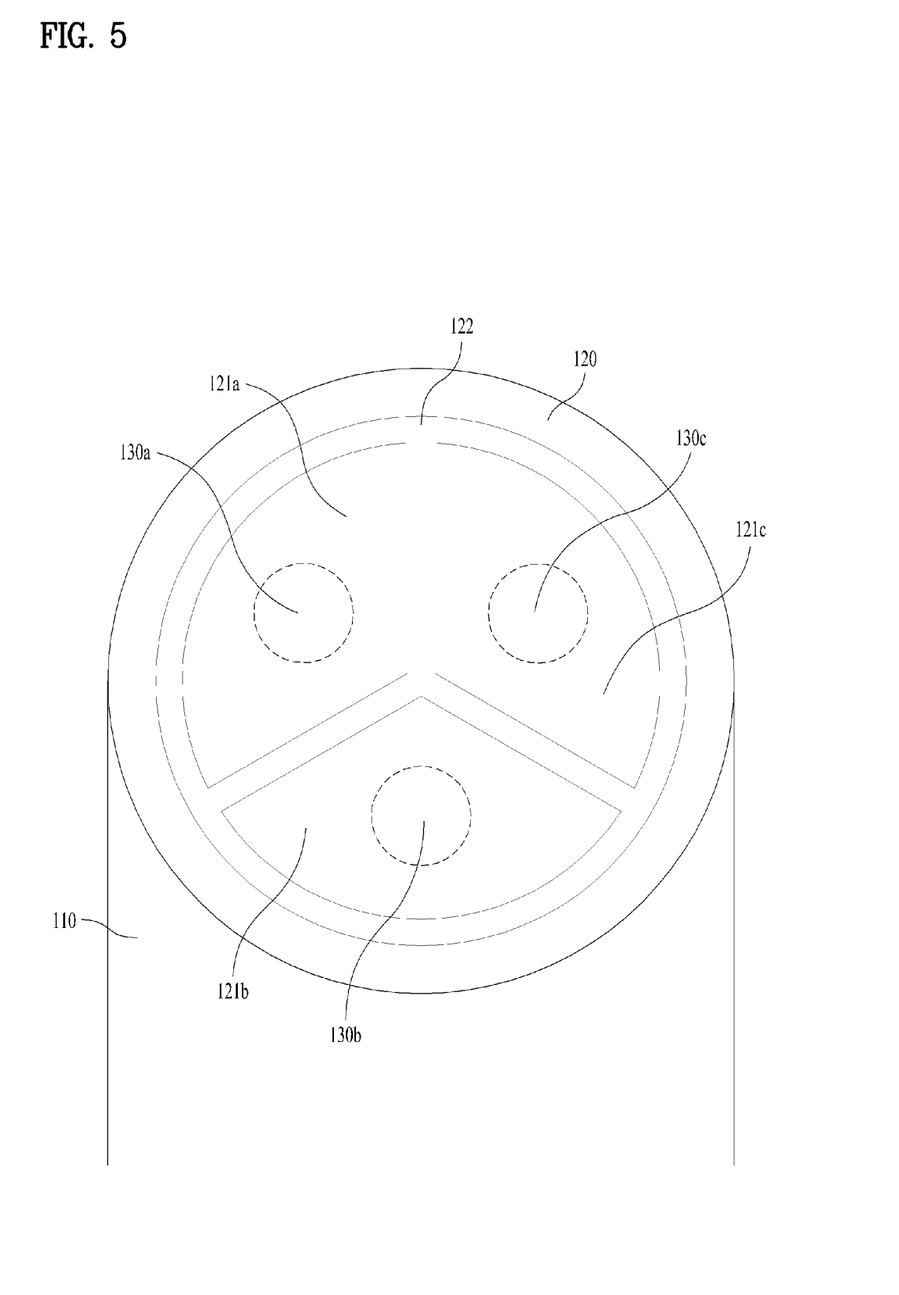
FIG. 5 is a front diagram showing another embodiment of a head part of a skin care device related to the present disclosure.

FIG. 4 is a diagram showing another embodiment of a head part 120 of a skin care device 100 related to the present disclosure, and FIG. 5 is a front diagram showing another embodiment of the head part 120 of the skin care device 100 related to the present disclosure.

Referring to FIG. 4 and FIG. 5, a skin contact plate 121 of a skin care device may have a sector shape generated from sectoring a circular shape. As shown in FIG. 5, the skin contact plate may be divided into three equal parts or more.

Alternatively, circular skin contact plates 121 may be disposed side by side. According to the present embodiment, unlike the former embodiment, one skin contact plate 121 may be formed to have thickness enough for a vibrator to be seated thereon and, as shown in FIG. 4, a vibrator may be directly seated on the skin contact plate 121. According to the former embodiment, a size of the head part 120 can be reduced but thickness thereof increases. On the contrary, according to the present embodiment, the thickness of the head part 120 can be reduced.

As mentioned in the description of the former embodiment, sine the connecting part 122 of the ductile material is inserted between the skin contact plates 121, each of the skin contact plates 121 may vibrate with ultrasonic wave of a different frequency. As shown in FIG. 5, the connecting part 122 may be provided between the case forming the exterior of the head part 120 and the skin contact plate 121 as well as between a plurality of the skin contact plates 121.

As the connecting part 122 has elasticity, it may reduce interference between vibrations applied to the skin contact plates 121, respectively and each of the skin contact plates 121 may move individually. If each of the skin contact plates 121 moves individually, it may be inclined at a difference angle along a curved surface of a face, whereby the effect of adherence between the skin contact plate 121 and a user skin can be increased.

Figure 6:
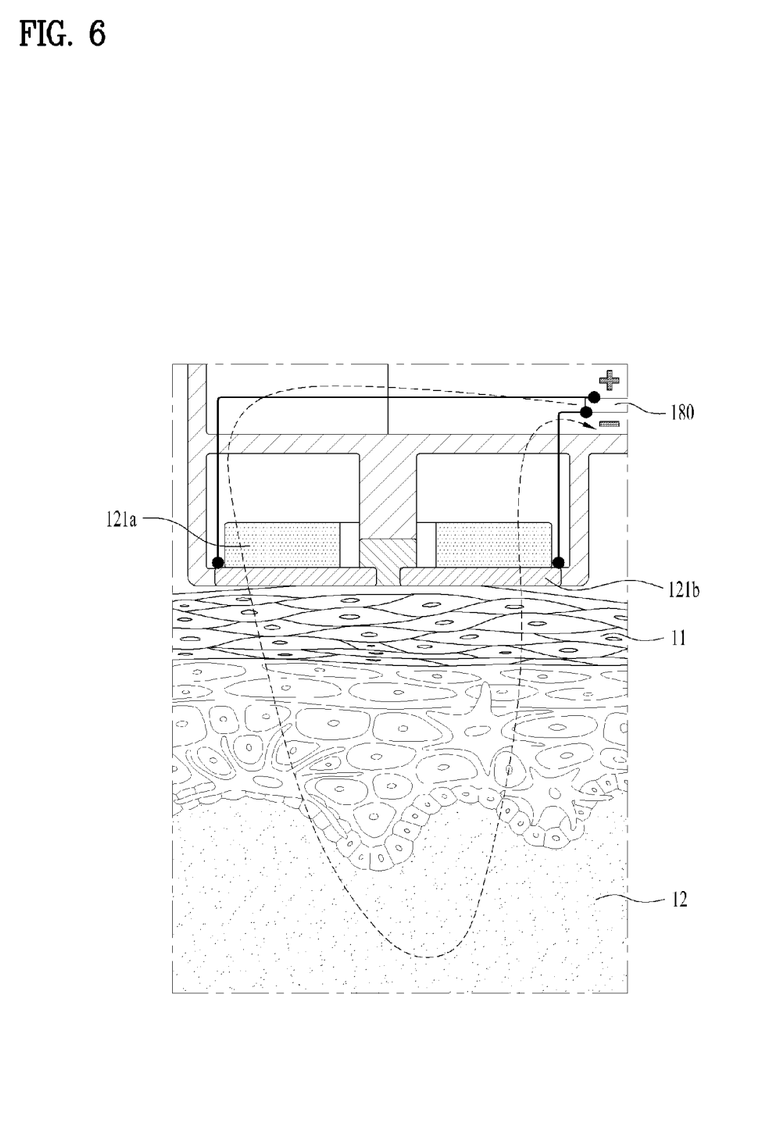
FIG. 6 is an exploded perspective diagram of a tip head of a skin care device related to the present disclosure.

FIG. 6 is an exploded perspective diagram of a tip head of the skin care device 100 related to the present disclosure. The skin contact plate 121 of the present disclosure is formed of conductive material and has one pole connected to the controller 180. Namely, the first skin contact plate 121a is connected to the + pole and the second skin contact plate 121b is connected to the − pole. If there are four or more skin contact plates 121, each of the skin contact plates 121 is connected to one pole.

The application of microcurrent to the user's skin improves the skin penetration effect of the vitamin-like molecules with polarity along the current, allowing cosmetics ingredients to pass through the epidermis 11 to the dermis 12. The + and − poles should be connected to separate conductors as the + and − pole connections to one electrode cause the current to flow back to the opposite polar direction rather than through the user's body.

As the conventional skin contact plate 121 consists of one conductor, it uses the principle that current flows through the skin when held by hand in a manner of exposing the electrode part to the grip part 110. However, since the present disclosure includes a plurality of skin contact parts, if they are connected to different poles, respectively, as shown in FIG. 6, the current flows from the first skin contact plate 121a to the second skin contact plate 121b through the skin.

The skin care device 100 of the present disclosure does not need to have a separate electrode part provided to the grip part 110. As current passes through only the area adjacent to a contacted skin, the cosmetics ingredients can penetrate the skin without the current needlessly passing through a body.

As described above, according to at least one of embodiments of the present disclosure, the absorption rate of cosmetics mixed with different ingredients can be raised. In addition, a user can be relieved of the inconvenience of holding onto and using a separately provided electrode.

Those skilled in the art will appreciate that the present disclosure may be carried out in other specific ways than those set forth herein without departing from the spirit and essential characteristics of the present disclosure.

The above embodiments are therefore to be construed in all aspects as illustrative and not restrictive. The scope of the disclosure should be determined by the appended claims and their legal equivalents, not by the above description, and all changes coming within the meaning and equivalency range of the appended claims are intended to be embraced therein.

What is claimed is:

1. A skin care device, comprising:
   a body including a grip part for being gripped by a user and a head part located at an end portion of the grip part;
   a plurality of skin contact plates located at an end portion of the head part;
   wherein the plurality of skin contact plates include a first skin contact plate having a circular shape and a second skin contact plate having a ring shape located around a circumference of the first skin contact plate;
   a support plate located on a backside of the second skin contact plate in a manner of being spaced apart in a prescribed distance;
   a connecting leg connecting the support plate and the second skin contact plate together;
   a plurality of vibrators providing vibration to the plurality of skin contact plates; and
   a controller supplying current to the plurality of skin contact plates and controlling the plurality of vibrators,
   wherein a + pole of the controller is connected to the first skin contact plate and a − pole of the controller is connected to the second skin contact plate; and
   wherein the plurality of vibrators comprise a first vibrator providing the vibration by being coupled to a backside of the first skin contact plate and a second vibrator seated on the support plate to provide the vibration to the second skin contact plate.

2. The skin care device of claim 1, wherein each of the plurality of vibrators provides the vibration of a different frequency.

3. The skin care device of claim 1, wherein the connecting leg has a cylindrical shape connected to the second skin contact plate in the ring shape at a plurality of points and wherein electric wire connects the first vibrator, the first skin contact plate and the controller passes through the connecting leg.

4. The skin care device of claim 1, wherein the plurality of skin contact plates are inclined at different angles, respectively.

5. The skin care device of claim 1, further comprising a connecting part connecting the plurality of skin contact plates in between and having a variable shape.

6. The skin care device of claim 5, wherein the plurality of skin contact plates include conductive material and wherein the connecting part includes insulating material to electrically divide the plurality of skin contact plates from each other.

7. The skin care device of claim 5, wherein the connecting part is formed of ductile material.

\* \* \* \* \*